United States Patent [19]

O'Donnell et al.

[11] Patent Number: 5,064,507
[45] Date of Patent: Nov. 12, 1991

[54] DISTILLATION PROCESS FOR RECOVERY OF HIGH PURITY PHENOL

[75] Inventors: Michael S. O'Donnell, Colonial Heights; Lamberto Crescentini, Chester, both of Va.

[73] Assignee: Allied-Signal Inc., N.J.

[21] Appl. No.: 588,868

[22] Filed: Sep. 27, 1990

[51] Int. Cl.⁵ .......................... B01D 3/32; C07C 37/76
[52] U.S. Cl. ........................................ 203/34; 203/35; 203/37; 203/38; 203/83; 203/88; 203/DIG. 19; 568/749; 568/754
[58] Field of Search ...................... 203/38, 34, 35, 92, 203/93, 96, 97, DIG. 19, 76, 83, 88; 568/754, 749

[56] References Cited

U.S. PATENT DOCUMENTS

| | | | |
|---|---|---|---|
| 3,140,318 | 7/1964 | Sodomann et al. | 203/38 |
| 3,322,651 | 5/1967 | Nielsen | 203/38 |
| 3,692,845 | 9/1972 | Cheema et al. | 568/754 |
| 4,298,765 | 11/1981 | Cochran et al. | 568/754 |
| 4,532,012 | 7/1985 | Khonsari et al. | 568/754 |
| 4,634,796 | 1/1987 | Suciu et al. | 568/754 |
| 4,851,086 | 7/1989 | Khonsam et al. | 203/45 |

Primary Examiner—Bascomb, Jr., Wilbur

[57] ABSTRACT

High purity phenol is obtained from cleavage of cumene hydroperoxide by treating the crude phenol product stream in a first treatment zone with an amine, a coarse distillation to obtain an overhead stream comprising phenol, alpha-methyl styrene, cumene, and impurities, and steam distillation of the overhead stream in combination with addition of an amine to the steam distillation column for a second amine treatment step.

28 Claims, 2 Drawing Sheets

DISTILLATION PROCESS FOR RECOVERY OF HIGH PURITY PHENOL

FIELD OF THE INVENTION

This invention relates to the production of phenol, and more particularly, to the production of high purity phenol.

DESCRIPTION OF RELATED ART

Phenol may be produced from cumene by the oxidation of cumene to cumene hydroperoxide, followed by cleavage of the hydroperoxide to phenol and acetone.

In such a process, the reaction product is introduced into a separation and recovery system wherein the crude product is initially treated in a distillation column to separate acetone byproduct from the remaining mixture. The acetone-free product is then introduced into a further distillation column which operates to separate cumene from the remaining product. Optionally, the cumene recovery column can be operated to recover alpha-methylstyrene (AMS) with the cumene. If the AMS is not recovered with the cumene, the product remaining from the cumene column is introduced into a crude AMS column to separate AMS from the remaining mixture.

The product remaining from the cumene recovery column, or the crude AMS column (in the case where AMS is recovered separately from the cumene), is then introduced into a phenol recovery column to separate phenol from remaining higher boiling components.

The thus recovered crude phenol includes impurities such as acetol, mesityl oxide (MO), 2-phenyl-propionaldehyde (2PPA), acetophenone (AP), 2- and 3-Methyl-benzofurans (collectively or individually MBF), oxygenated compounds (including various isomers of hexanone, heptanone, octanone, tetra-methyl pentanone—collectively or individually C6–C9 Ketones) and other compounds.

In one process, the crude phenol is chemically treated to reduce the amount of acetol and MO present in the crude phenol. Thus, for example, the crude phenol may be treated with an amine, followed by addition of acid or acid anhydride, as disclosed, for example in U.S. Pat. No. 3,692,845.

In a second process disclosed in U.S. Pat. No. 4,298,765, the crude phenol is first treated with an amine, and optionally an acid or acid anhydride, and then distilled in the presence of water to recover from the top of the column a phenol water azeotrope containing the majority of MBF and other impurities present in the treated phenol. The resulting product is referred to as high purity phenol. The water in the overheads is treated, after an initial separation from a phenol rich phase, with a solvent to extract organics therefrom, or the phenol-water mixture is treated with a solvent followed by phase separation of organics. In such a process, a significant portion of the phenol present in the overhead is recovered in the organic phase, and it is necessary to separately treat the organic phase to recover such significant portion of phenol. Such recovery increases overall costs.

In a third process disclosed in U.S. Pat. No. 4,532,012, phenol containing MBF as an impurity, is processed by steam distillation in the presence of water and a water immiscible organic extraction solvent for MBF (at least one member selected from the group consisting of AMS, cumene). The resulting light overhead product is separated into an aqueous phase (containing phenol and water and is recycled to same distillation), and an organic phase containing extraction solvent, some phenol and impurities (including MBF). The operation of this process, (including aqueous phase recycle) results in reduced costs. The resulting product is referred to as high purity phenol and contains no greater than 10–25 PPM MBF.

In a fourth process disclosed in U.S. Pat. No. 4,634,796), crude phenol containing AMS byproduct, MBF, MO, acetol and other impurities is first treated with a base without acidification (to remove MO, acetol as in U.S. Pat. No. 3,692,845 described above), then subjected to steam distillation in the presence of byproduct AMS (which acts as an extraction solvent as in U.S. Pat. No. 4,532,012 described above), next treated with an acid, and lastly distilled in a high purity phenol column to recover high purity phenol. The acid treatment prior to the final distillation: (1) reduces the formation of AMS derived impurities (some of which decompose in the final distillation and result in increased levels of AMS in the high purity product), and therefore allows a decrease in the final column lights (pasteurizing) cut, (2) results in higher AMS recovery yield in contrast to use of acid prior to steam distillation where AMS is still present, and, (3) imparts improved color stability to the high purity phenol product.

In a fifth process, disclosed in U.S. Pat. No. 4,851,086), crude phenol containing AMS and/or cumene byproduct, MBF, MO, acetol and other impurities is first subjected to steam distillation and then distilled in a final product column to produce high purity phenol. The AMS and/or cumene byproducts (present during the steam distillation step of the process function as extraction solvent U.S. Pat. No. 4,532,012) and are recovered and retained. The use of AMS and/or cumene byproduct in the steam distillation column allows reductions in costs and elimination of a column normally used in phenol production plants (where phenol is produced by oxidation of cumene to cumene hydroperoxide, followed by cleavage of cumene hydroperoxide to phenol and acetone).

The present invention is particularly advantageous in that impurity levels in the high purity phenol product produced are greatly reduced relative to the existing technologies hereinabove discussed, with low overall costs. More particularly, the present invention provides a high purity phenol product containing greatly reduced levels of total carbonyl impurities, MO, MBF, and ketones. Ultra high purity phenol containing less than 25 ppm total impurities (measured by gas chromatography/ mass spectrometry) and a total carbonyl analysis of less than 15 ppm (expressed as mesityl oxide) can be obtained by the process of this invention.

SUMMARY OF THE INVENTION

In a process for producing high purity phenol wherein alpha-methyl styrene (AMS) is produced as a by-product, the improvement comprising:

recovering a crude phenol product stream which includes AMS produced as a by-product in an amount of at least 0.5 weight percent and no greater than 10 weight percent, based on weight of phenol, and further includes acetol, 2-phenyl-propionaldehyde (2PPA), methyl-benzofuran (MBF), mesityl oxide (MO), and carbonyl impurities;

treating said crude phenol product stream in a first treatment zone with an amine to convert acetol and 2PPA to higher boiling components;

distilling said treated phenol product stream to separate higher boiling components and an overhead stream comprising phenol, AMS, and impurities including MBF, MO, and carbonyl compounds;

steam distilling said overhead stream in a steam distillation column with a water to phenol ratio of at least 0.2:1 and no greater than 1.2:1 to recover a light product comprising phenol, water, AMS, MBF and carbonyl compounds and a heavy product comprising phenol having a reduced quantity of MBF, AMS, and carbonyl compounds, relative to said overhead stream;

said steam distillation step additionally comprising a second amine treatment step whereby an effective amount of an amine is added to the lower portion of said steam distillation column to convert MO and carbonyl impurities to heavy and light impurities;

and distilling the heavy product from the steam distillation step to recover high purity phenol and a bottoms product containing heavies and unreacted amine.

In a preferred embodiment the bottoms product containing heavies and unreacted amine is recycled to the first treatment zone to provide the amine. The high purity phenol recovered can optionally be treated with a strong non-volatile acid or acid resin and subjected to a flash distillation.

DESCRIPTION OF THE PREFERRED EMBODIMENT

Figure 1:
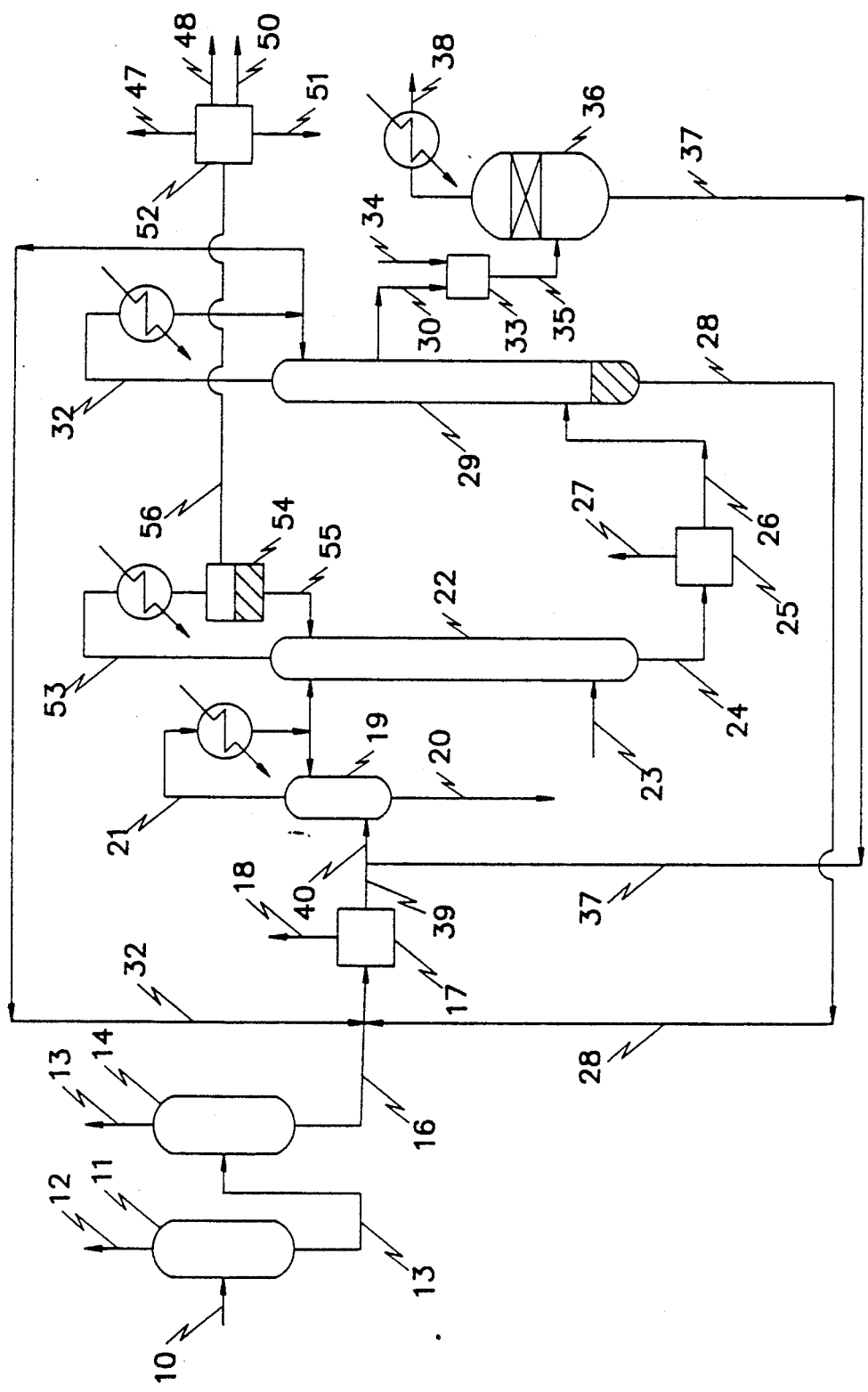
FIG. 1 is a schematic representation of a preferred embodiment of the present invention.

Referring now to the drawing, a reaction effluent recovered from the reaction section of a procedure for producing phenol by the oxidation of cumene to cumene hydroperoxide, followed by acid cleavage of the hydroperoxide to phenol and acetone in line 10, includes, as principal components, phenol, acetone, cumene, alphamethylystyrene (AMS), and as primary impurities, MBF, acetophenone (AP), dimethylphenyl carbinol (DMPC), acetol, mesityl oxide (MO), oxygenated compounds (including various isomers of hexanone, heptanone, octanone, tetra-methyl-pentanone—collectively or individually C6–C9 Ketones), 2-phenyl-propionaldehyde(2PPA), and other compounds including various carbonyl compounds, and is introduced into an acetone recovery column designated as 11, to recover acetone as an overhead through line 12, and a bottoms product through line 13.

The bottoms product in line 13 is introduced to a cumene recovery column designated as 14, operated to recover cumene and AMS overhead through line 15. The cumene column 14 is specifically operated in a manner such that there is AMS present in the bottoms product recovered through line 16 for use, as hereinafter described, in the procedure of the present invention directed to separation of MBF and other impurities from phenol. In general, there is also some cumene in the bottoms product.

The bottoms in line 16 is then combined with recycled phenol (final product column lights/pasteurizing cut) containing trace impurities in line 32a and recycled phenol (product column bottoms) containing a non-volatile amine and other heavies in line 28, and then introduced into a chemical treatment zone, designated 17, preferably a plug flow type reactor. The treating agent, an amine, is preferably an aliphatic polyamine such as hexamethylenediamine and methylpentanediamine. The chemical treatment is effected in a manner such that acetol, 2PPA, and MO are converted to higher boiling components. Light impurities which may be generated (such as ammonia from amine decomposition, etc.) are vented through line 18. In accordance with the present invention, the chemical treatment is effected in a manner such that the AMS and cumene remain in the liquid phase.

The treated phenol in line 39 is then combined with recycled phenol containing heavy impurities in line 37 and introduced through line 40 to a column designated 19, in which a coarse distillation is performed, in order to separate higher boiling components (tar) in line 20, and an overhead stream in line 21. Line 37 is recycled into line 39 rather than into line 16 to avoid chemical reaction (deactivation) of the acid and the amine from line 28 before the preferred reaction in zone 17 can occur. Acids and a portion of the carbonyl compounds present in the recycled phenol in line 37 are converted to high boiling compounds by the amine and are separated to line 20. The higher boiling components in line 20 may be further treated to recover more of the phenol contained therein.

The overhead stream from column 19 removed through line 21 includes phenol, as well as cumene and AMS which will function as organic extraction solvent in the separation zone 54 of the subsequent steam distillation step, and impurities including MBF, MO, acetone, C6–C9 ketones and other impurities. The phenol in line 21 is essentially free of materials which boil higher than AP. A portion of stream 21 is supplied as reflux to the top of column 19. The remaining portion of phenol in line 21a is then introduced, along with an aqueous phase in line 55 (obtained as hereinafter described), to the upper portion of a steam/water azeotropic column designated 22.

The column 22 is operated at a temperature and pressure to separate impurities from phenol. The water to phenol ratio in the column is at least 0.2:1 and no greater than 1.2:1, preferably at least 0.3:1 and no greater than 1.0:1, most preferably at least 0.4:1 and no greater than 0.8:1. Water, phenol, the cumene AMS solvent and impurities such as MBF and other carbonyl compounds (including C6–C9 Ketones) are recovered from the top of the column through line 53. An amine with low volatility is also introduced at 23 to the lower portion of column 22. The amine is preferably hexamethylenediamine. Suitable heating is provided such that a bottom stream essentially free of water is withdrawn through line 24. The bottom stream (line 24) is comprised of phenol, the amine added through line 23, and impurities including AP, MO, and other impurities not effectively separated to the overhead in line 53. The overheads in line 53 are cooled to effect condensation, and the condensed overhead is introduced into a separation zone designated 54, to separate the condensed overhead into an aqueous phase and an organic phase. The AMS and cumene present act as an extraction solvent, and provide improved separation of phenol, and impurities including MBF, carbonyl compounds, C6–C9 ketones and other impurities.

The aqueous phase which is comprised of phenol and water, and which contains a small amount of impurities, is fed back as reflux to the column 22 through line 55.

The organic phase (oil phase), stream 56, is supplied to an AMS recovery system, represented by box 52 where AMS and cumene are recovered by caustic treatment followed by distillation with both heavy and light stream purges.

Figure 2:
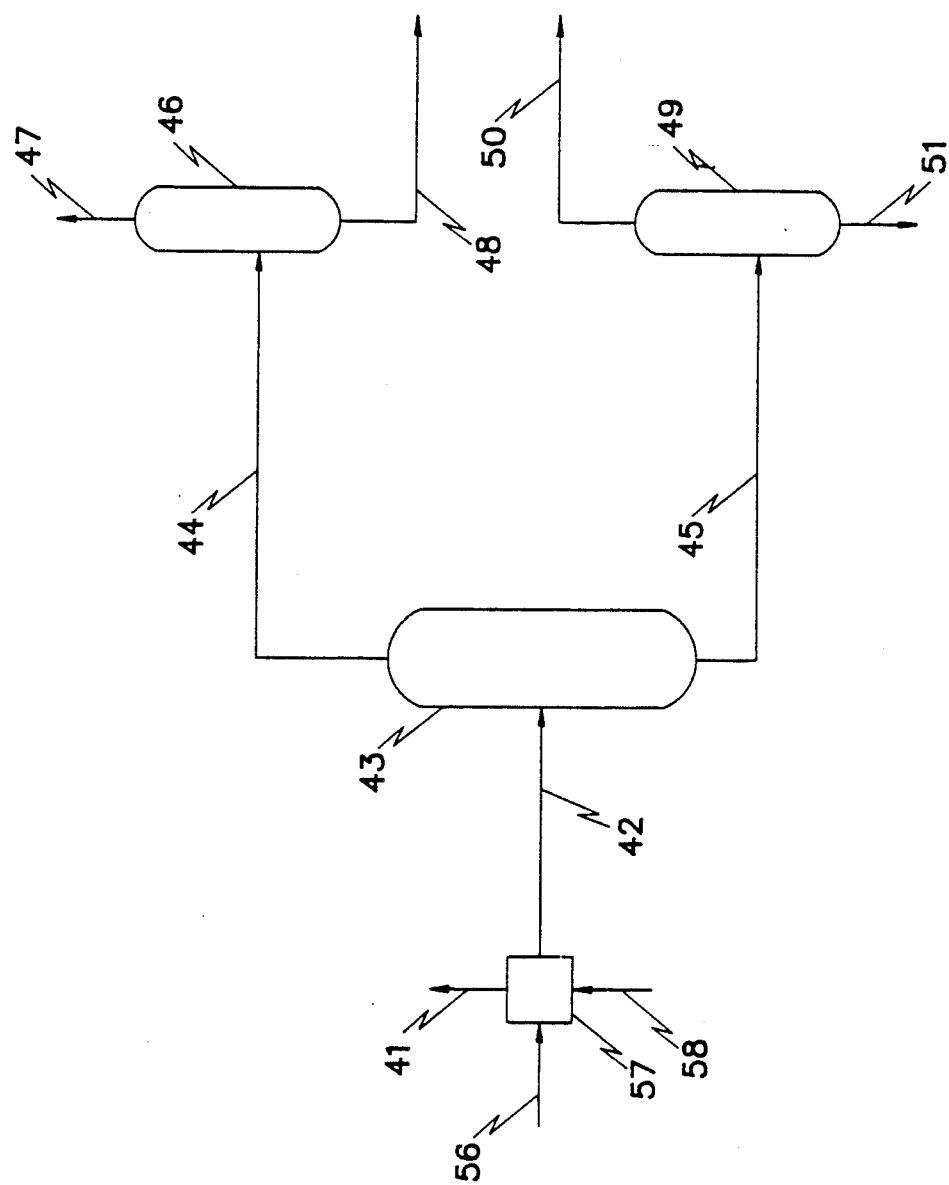
FIG. 2 is a schematic representation of the invention showing a preferred AMS recovery system.

A preferred AMS recovery system is illustrated in FIG. 2. The organic phase, comprised of the AMS and cumene (which act as an extraction solvent in the separation zone 54 of FIG. 1.), as well as phenol, and impurities including MBF, carbonyl compounds, C6–C9 ketones and other impurities is withdrawn from the separation zone 54 of FIG. 1 through line 56 and introduced into zone 57, wherein the organic phase is contacted with an aqueous base, such as sodium hydroxide, introduced through line 58 for the purpose of converting any phenol into sodium phenate, which is water soluble and remains in an aqueous phase, while MBF and other impurities are not, whereby they remain in the organic phase.

Aqueous sodium phenate is recovered from zone 57 through line 41 for subsequent treatment to recover phenol.

The organic phase, which is now essentially free of phenol, is withdrawn from zone 57 through line 42 for further treatment.

For example, as shown in FIG. 2, the organic phase in line 42 is introduced to distillation column 43, where AMS and heavier compound are separated as a bottoms product through line 45, and cumene and lighter compounds are recovered as a overhead product through line 44. The overheads product in line 44 is introduced to distillation column 46 to separate light impurities (including MO, etc.) present in line 44 to the overheads product through line 47, and produce a bottoms product (cumene) through line 48 for recycle, as feed to the phenol production. Line 45 is introduced to distillation column 49 to separate heavy impurities (including MBF, AP, etc.) present in line 45 to the bottoms product through line 51, and produce an overhead product (AMS) through line 50. The AMS recovered is of purity suitable either for sales or recycle.

The phenol, recovered from the azeotropic steam stripping distillation column 22 through line 24 is then introduced into a chemical treatment zone, designated 25, where the amine (previously added to the lower portion of the azeotropic steam stripping column 22) converts difficult to remove impurities (including MO) to heavier compounds. Light impurities which may be generated (such as ammonia from amine decomposition, etc.) are vented through line 27. In accordance with the present invention, the chemical treatment is effected in a manner such that the phenol remains in the liquid phase, and volatiles concentrate in the vapor phase and are removed through line 27. This illustrates a preferred manner of carrying out the process, but it must be observed that other appropriate means are available, such as providing sufficient residence time in the column sump or reboiler, then venting through the column.

The treated phenol is removed from the treatment zone through line 26, and then introduced into the lower portion of a phenol recovery column, designated 29. The column is operated in a manner to separate impurities lighter than phenol to an overheads (pasteurizing cut) product through line 32, and impurities heavier than phenol to a bottoms product through line 28, both being recycled as hereinabove discussed (where lines 16, 28, and 32a are combined and introduced to chemical treatment zone 17). A portion of line 32 is supplied as reflux to the top of column 29. The bottoms product withdrawn from column 29 through line 28 is comprised of phenol, the amine added previously through line 23, and other heavy impurities.

A high purity phenol overhead product is recovered from column 29, through line 30, is then optionally introduced to a chemical treatment zone, designated 33, where the phenol is treated with an acid, to reduce the quantity of carbonyl compounds (including C6–C9 ketones) and volatile bases (including ammonia from amine decomposition), and improve the phenol color stability. For example, as shown in FIG. 1, a strong non-volatile acid is introduced through line 34, along with the phenol in line 30, to the treatment zone 33. The acid is preferably 4-hydroxy-benzenesulfonic acid, sulfuric acid, or para toluenesulfonic acid. The treated phenol removed from treatment zone 33 through line 35 therefore contains any acid added through line 34. Alternatively, (not shown) the treatment could be effected in a manner as to contact the phenol introduced through line 30 with an acid resin or other means in treatment zone 33. A typical acid resin consists of sulfonated cross-linked polystyrene beads.

The treated phenol, withdrawn from zone 33 through line 35, is then optionally introduced to a distillation column, designated 36, where a flash distillation operation is performed with or without a lights/pasteurizing cut as described for column 29. A high purity phenol product is recovered from column 36 through line 38. The bottoms product recovered from column 36 through line 37 is comprised mainly of phenol, acid added through line 34 to treatment zone 33, and other impurities, and is recycled as hereinabove discussed (being combined with line 39 and introduced to column 19).

Although the invention has been described with respect to a preferred embodiment in the accompanying drawing, it is to be understood that the scope of the invention is not limited to such an embodiment. Numerous modifications should be apparent to this skilled in the art from the teaching therein.

In the following examples, analysis for impurities is by gas chromatography/massspectrometry. Total carbonyl analysis was obtained by measuring spectrophotometrically color developed on addition of 2,4-dinitrophenylhydrozine (expressed as mesityl oxide).

The invention will be described with respect to the following two (2) examples; however, the scope of the invention is not limited thereby:

EXAMPLE 1

Product from the bottom of cumene recovery column (column 14 of the drawing) was treated with about 1000 ppm hexamethylenediamine (HMDA) to effect a partial removal of carbonyl impurities. The heavy boilers present in the original phenol or formed during the chemical treatment were separated by a coarse distillation of the chemically treated product (column 19 of the drawing).

The overhead product from the coarse distillation was subjected to distillation with water, with HMDA being continuously added to the lower portion of the distillation column (column 22 of drawing). The bottom product from the azeotropic distillation was held in a treatment zone (zone 25 of the drawing) for about 2 hours to allow complete treatment by the amine.

The azeotropic distillation was accomplished using a continuously operating 2" ID, vacuum jacketed, Oldershaw column with 55 actual trays. Phenol and water were metered, mixed, preheated to 90 C., and fed to the top tray (tray 55, counting from bottom) of the column. A solution of HMDA in water was metered and continuously fed to tray 15 (counting from the bottom) of the column. Amount of HMDA added was 0.14% (1400 ppm) of feed in line 21a. The vapors which leave the top (tray 55) of the column are condensed and separated into an aqueous and an organic phase.

The feed and products corresponding to a period of eight (8) hours of continuous operation were collected and analyzed. The azeotropic column was fed 990 ml per hour overhead product from the coarse distillation and 780 ml per hour distilled water (a water:phenol ratio of 0.79:1). The composition and flow rates of the various streams is reported in Table I.

TABLE I

|  | Azeo Feed | Treated Bottoms | Organic Phase | Aqueous Phase |
|---|---|---|---|---|
| Flow ml/hr | 990 | 870 | 60 | 840 |
| Total Carbonyl Analysis | NA | NA | NA | NA |
| Acetone | 125 | 9 | NA | NA |
| MO | 20 | ND | 400 | NA |
| Cumene | 9300 | ND | 14% | 85 |
| Acetol | 65 | ND | 3700 | ND |
| AMS | 2.4% | 5 | 38% | 266 |
| MBF | 31 | ND | 482 | ND |
| 2PPA | ND | ND | ND | ND |
| AP | 4400 | 3500 | 5900 | 32 |
| DMPC | 250 | 230 | 240 | ND |
| Ketones (C6-C9) | NA | NA | NA | NA |
| Phenol | Balance | Balance | Balance | 5.7% |

All concentrations in ppm except as noted
ND = Not detected (less than 5 ppm)
NA = Not analyzed
DMPC = dimethylphenyl carbinol

EXAMPLE 2

Chemically treated phenol being previously prepared by the method of Example 1 above (line 26 of the drawing), was distilled under vacuum (column 29 of the drawing), recovering an overhead phenol product (line 30 of the drawing), an overhead pasteurizing cut (line 32 of the drawing), and a bottoms product (line 28 of the drawing). The distillation was accomplished using a continuously operating 2" ID, vacuum jacketed, Oldershaw column with 55 actual trays, the feed being introduced at tray 15 (counting from the bottom), the overhead phenol product withdrawn from tray 45 (counting from the bottom), and the pasteurizing cut withdrawn from the top of the tower (tray 55, counting from the bottom).

The overhead phenol product produced (line 30 of the drawing) was then further treated by addition of 400 parts per million (ppm) of hydroxy-benzenesulfonic acid (previously prepared by reaction of sulfuric acid with phenol), allowing 120 minutes reaction time at 160 C. The thus treated phenol was then flash distilled under vacuum, to produce high purity product phenol (line 38 of the drawing). The composition and flow rates of the various streams is reported in Table II below.

TABLE II

|  | Distillation Feed | Overhead Prod | Past. Cut | Bottoms | Acid Treated Finished Product |
|---|---|---|---|---|---|
| Flow ml/hr | 970 | 710 | 50 | 210 | — |
| Total Carbonyl Analysis | NA | 13 | NA | NA | 5 |
| Acetone | 9 | ND | NA | ND | ND |
| MO | ND | ND | ND | ND | ND |
| Cumene | ND | ND | 8 | ND | ND |
| Acetol | ND | ND | NA | ND | ND |
| AMS | 5 | 3 | 150 | ND | ND |
| MBF | ND | ND | ND | ND | ND |
| 2PPA | ND | ND | ND | NA | ND |
| AP | 3500 | ND | ND | NA | ND |
| DMPC | 230 | ND | ND | NA | ND |
| Ketones (C6-C9) | NA | 3 | 3 | 45 | 0.5 |
| Phenol | Balance | Balance | Balance | Balance | Balance |

All concentrations in ppm
ND = Not detected (Less than 0.5 ppm)
NA = Not analyzed

COMPARATIVE EXAMPLE

In a process operated in accordance with U.S. Pat. No. 4,851,086 (without optional acid treatment via acid in line 19 of the drawing and with a water/phenol ratio of 0.4 in column 26 of the drawing) conducted in continuously operated pilot plant equipment (2 inch ID Oldershaw column, vacuum jacketed) high purity phenol was produced with purity as shown in Table III, which is compared with the purity of the phenol produced from examples 1 and 2 above. The purity of the phenol produced by the process of the present invention is shown to be greatly superior to that of the U.S. Pat. No. 4,851,086 process.

TABLE III.

|  | High Purity Phenol (Comparative) | Present Invention (Ex. 2) |
|---|---|---|
| Total Carbonyl Analysis | 32 | 5 |
| Acetone | 1 | ND |
| MO | 10 | ND |
| Cumene | ND | ND |
| Acetol | 0.3 | ND |
| AMS | 1 | ND |
| MBF | 8 | ND |
| 2PPA | ND | ND |
| AP | ND | ND |
| DMPC | ND | ND |
| Ketones (C6-C9) | 14 | 0.5 |

All concentrations in ppm
ND = Not detected (Less than 0.5 ppm)

Numerous modifications and variations of the present invention are possible in light of the above teachings, and, therefore, within the scope of the appended claims, the invention may be practiced otherwise than as particularly described.

What is claimed:

1. In a process for producing high purity phenol wherein alpha-methyl styrene (AMS) is produced as a by-product, the improvement comprising:
   recovering a crude phenol product stream which includes AMS produced as a by-product in an amount of at least 0.5 weight percent and no greater than 10 weight percent, based on weight of phenol, and further includes acetol, 2-phenyl-propionaldehyde (2PPA), methyl-benzofuran (MBF), mesityl oxide (MO), and carbonyl impurities;

treating said crude phenol product stream in a first treatment zone with an amine to convert acetol and 2PPA to higher boiling components;

distilling said treated phenol product stream to separate higher boiling components and an overhead stream comprising phenol, AMS, and impurities including MBF, MO, and carbonyl compounds;

steam distilling said overhead stream in a steam distillation column with a water to phenol ratio of at least 0.2:1 and no greater than 1.2:1 to recover a light product comprising phenol, water, AMS, MBF and carbonyl compounds and a heavy product comprising phenol having a reduced quantity of MBF, AMS, and carbonyl compounds, relative to said overhead stream;

said steam distillation step additionally comprising a second amine treatment step whereby an effective amount of an amine is added to the lower portion of said steam distillation column to convert MO and carbonyl impurities to heavy and light impurities;

and distilling the heavy product from the steam distillation step to recover high purity phenol and a bottoms product containing heavies and unreacted amine.

2. The process of claim 1 wherein the bottoms product containing heavies and unreacted amine is recycled to the first treatment zone, thereby providing said amine to said first treatment zone.

3. The process of claim 1 wherein the amine added in the first treatment zone and the second amine treatment step is selected from the group consisting of hexamethylenediamine and methylpentanediamine.

4. The process of claim 1 wherein the crude phenol product stream further includes cumene.

5. The process of claim 1 wherein the water to phenol ratio in the steam distillation step is at least 0.3:1 and no greater than 1.0:1.

6. The process of claim 5 wherein the water to phenol ratio is at least 0.4:1 and no greater than 0.8:1.

7. The process of claim 6 wherein the bottoms product containing heavies and unreacted amine is recycled to the first treatment zone, thereby providing said amine to said first treatment zone.

8. The process of claim 2 wherein the heavy product recovered from said steam distillation step contains no greater than 10 ppm MBF.

9. The process of claim 8 wherein the heavy product contains no greater than 15 ppm carbonyl compounds.

10. The process of claim 9 wherein the high purity phenol recovered by distilling the heavy product contains no greater than 25 ppm total impurities.

11. The process of claim 2 wherein said crude phenol product stream includes no greater than 7 weight percent AMS.

12. The process of claim 1 wherein the high purity phenol recovered by distilling the heavy product is treated with a strong nonvolatile acid or acid resin.

13. The process of claim 12 wherein the acid is hydroxy-benzenesulfonic acid or sulfuric acid.

14. The process of claim 2 wherein the high purity phenol recovered by distilling the heavy product is treated with a strong nonvolatile acid or acid resin.

15. The process of claim 14 wherein the acid is hydroxy-benzenesulfonic acid or sulfuric acid.

16. The process of claim 7 wherein the high purity phenol recovered by distilling the heavy product is treated with a strong nonvolatile acid or acid resin.

17. The process of claim 16 wherein the acid is hydroxy-benzenesulfonic acid or sulfuric acid.

18. The process of claim 16 wherein the acid is an acid resin.

19. The process of claim 10 wherein the high purity phenol recovered by distilling the heavy product is treated with a strong nonvolatile acid or acid resin.

20. The process of claim 19 wherein the acid is hydroxy-benzenesulfonic acid or sulfuric acid.

21. The process of claim 12 wherein said high purity phenol is subjected to flash distillation after said acid treatment.

22. The process of claim 14 wherein said high purity phenol is subjected to flash distillation after said acid treatment.

23. The process of claim 16 wherein said high purity phenol is subjected to flash distillation after said acid treatment.

24. The process of claim 19 wherein said high purity phenol is subjected to flash distillation after said acid treatment.

25. In a process for producing phenol by oxidation of cumene to cumene hydroperoxide and cleavage of cumene hydroperoxide to phenol and acetone wherein alpha-methyl styrene (AMS) is produced as a by-product, the improvement comprising:

recovering a crude phenol product stream which includes some unreacted cumene, AMS produced as a by-product in an amount of at least 0.5 weight percent and no greater than 10 weight percent, based on weight of phenol, and further includes acetol, 2-phenyl-propionaldehyde (2PPA), methyl-benzofuran (MBF), mesityl oxide (MO), and carbonyl impurities;

treating said crude phenol product stream in a first treatment zone with an amine to convert acetol and 2PPA to higher boiling components;

distilling said treated phenol product stream to separate higher boiling components and an overhead stream comprising phenol, AMS, cumene, and impurities including MBF, MO, and carbonyl compounds;

steam distilling said overhead stream in a steam distillation column with a water to phenol ratio of at least 0.3:1 and no greater than 1.0:1 to recover a light product comprising phenol, water, cumene, AMS, MBF and carbonyl compounds and a heavy product comprising phenol having a reduced quantity of MBF, AMS, and carbonyl compounds, relative to said overhead stream;

said steam distillation step additionally comprising an amine treatment step whereby an effective amount of an amine is added to the lower portion of said steam distillation column to convert MO and carbonyl impurities to heavy and light impurities;

distilling the heavy product from the steam distillation step to recover high purity phenol and a bottoms product containing heavies and unreacted amine;

and recycling said bottoms product containing heavies and unreacted amine to the first treatment zone, thereby providing said amine to said first treatment zone.

26. The process of claim 25 wherein the high purity phenol recovered by distilling the heavy product is treated with hydroxybenzensulfonic acid or sulfuric acid.

27. The process of claim 26 wherein said high purity phenol is subjected to flash distillation after said acid treatment.

28. The process of claim 25 wherein the high purity phenol recovered by distilling the heavy product is treated with an acid resin.

* * * * *